(12) United States Patent  
Jovanovic et al.

(10) Patent No.: US 8,574,158 B2  
(45) Date of Patent: Nov. 5, 2013

(54) TIME OF FLIGHT ESTIMATION METHOD USING BEAMFORMING FOR ACOUSTIC TOMOGRAPHY

(75) Inventors: Ivana Jovanovic, Lausanne (CH); Ali Hormati, Chavannens (CH); Oliver Roy, Lausanne (CH); Martin Vetterli, Grandvaux (CH)

(73) Assignee: Ecole Polytechnique Federale de Lausanne, Lausanne (CH)

( * ) Notice: Subject to any disclaimer, the term of this patent is extended or adjusted under 35 U.S.C. 154(b) by 690 days.

(21) Appl. No.: 12/502,457

(22) Filed: Jul. 14, 2009

(65) Prior Publication Data

US 2010/0010351 A1    Jan. 14, 2010

Related U.S. Application Data

(60) Provisional application No. 61/080,358, filed on Jul. 14, 2008.

(51) Int. Cl.  
*A61B 8/00* (2006.01)  
*H04B 1/02* (2006.01)

(52) U.S. Cl.  
USPC ............................ 600/447; 600/448; 367/138

(58) Field of Classification Search  
USPC ........................................................ 600/447  
See application file for complete search history.

(56) References Cited

U.S. PATENT DOCUMENTS

| 4,222,274 | A |   | 9/1980 | Johnson |
|---|---|---|---|---|
| 4,317,369 | A |   | 3/1982 | Johnson |
| 4,395,909 | A |   | 8/1983 | Steinberg et al. |
| 5,343,404 | A | * | 8/1994 | Girgis ............................. 702/72 |
| 5,640,959 | A |   | 6/1997 | Hara et al. |
| 5,779,638 | A | * | 7/1998 | Vesely et al. .................. 600/437 |
| 6,475,150 | B2 |   | 11/2002 | Haddad |

(Continued)

FOREIGN PATENT DOCUMENTS

| EP | 1473562 | 11/2004 |
|---|---|---|
| FR | 2862520 | 5/2005 |

(Continued)

OTHER PUBLICATIONS

Ivana Jovanovic, Luciano Sbaiz, Martin Vetterli, Acoustic Tomography for Scalar and Vector Fields: Theory and Application to Temperature and Wind Estimation, American Meteorological Society Journal of Atmospheric and Oceanic Technology, 2008, pp. 1-15.

*Primary Examiner* — Tse Chen  
*Assistant Examiner* — Patricia Park  
(74) *Attorney, Agent, or Firm* — Blank Rome LLP

(57) ABSTRACT

It is disclosed an acoustic tomography method to improve the time of flight estimation, said method comprising the steps of: sequentially triggering a set of N transmitters so as to generate a sequence of N acoustic waves through a volume being scanned; receiving each of said acoustic waves after transmission through said volume with a set of M receivers, which are called received signals; delaying by varying delays the N different said received signals that each receiver receives from the N different transmitters, and adding them together to form a new received signal, which is called transmit-beamformed signal for that receiver; delaying by varying delays the M different said transmit-beamformed signals for each receiver and adding them together at each receiver to form a new signal, which we call transmit-receive-beamformed signal.

8 Claims, 3 Drawing Sheets

Time

(56) References Cited

U.S. PATENT DOCUMENTS

| | | |
|---|---|---|
| 6,721,235 B2 * | 4/2004 | Chiang et al. ............... 367/138 |
| 6,786,868 B2 | 9/2004 | Stotzka et al. |
| 2002/0080683 A1 * | 6/2002 | Chiang et al. ............... 367/138 |
| 2004/0167396 A1 | 8/2004 | Chambers et al. |
| 2006/0106307 A1 * | 5/2006 | Dione et al. ............... 600/437 |
| 2009/0105592 A1 * | 4/2009 | Yao ............... 600/447 |

FOREIGN PATENT DOCUMENTS

| | | |
|---|---|---|
| WO | WO-0230288 | 4/2002 |
| WO | WO-2004064619 | 8/2004 |
| WO | WO-2007115200 | 10/2007 |

* cited by examiner

Time

TIME OF FLIGHT ESTIMATION METHOD USING BEAMFORMING FOR ACOUSTIC TOMOGRAPHY

REFERENCE DATA

This application claims priority of the provisional U.S. application No. 61/080,358 dated from Jul. 14, 2008, the content whereof is hereby incorporated.

FIELD OF THE INVENTION

The present invention concerns an acoustic tomography method for time of flight estimation using beamforming. The invention concerns notably, but not exclusively, a method used in medical imaging and non-destructive testing.

DESCRIPTION OF RELATED ART

WO2007115200 describes a thermoacoustic tomography (TAT) method in which a part of the tissue is heated by some radiation (e.g. microwave) such that the expansion in the tissue generates acoustic signals. These acoustic signals which radiates from one small area of the tissue will be received by an array of receivers. The received signals are then processed to find the absorption rate of the tissue. Thermoacoustic tomography relies on the expansion of tissues when an acoustic wave is received. The tissue heating caused by the acoustic wave limit the use of the system, and makes any beamforming difficult.

This document suggests to find peaks in signals received by different receivers, and use the time position of those peaks for aligning the signals. It does not suggest using a reference signal for alignment.

U.S. Pat. No. 4,317,369 is an older document describing an acoustic tomography and blur reduction. In this document, a method for generating a reflection image is presented. The transmission tomography is used in order to correct and enhance the reflection image. The image reconstructed from the transmission tomography is the sound speed distribution inside the region of interest. The information about the sound speed is further used to find the rays from the transmitters to every point inside the region of interest and back to the receivers. Knowing the rays of sound speed propagation helps to correct the reflection image. In summary, this document talks about the transmission tomography as a tool to enhance the reflection tomography. Not many details about the transmission tomography are given. For example, this document does not suggest any transmit beamforming. There is a possibility of receive beamforming but only in the vertical direction (no horizontal beamforming).

U.S. Pat. No. 4,222,274 describes an ultrasound imaging apparatus comprising a ring of transducer arrays comprising transmitter arrays and receiver arrays.

US2004167396 describes an imaging method comprising many transducers surrounding a target region, transmitting from one transducer an acoustic pulse and receiving pulse-derived temporal data at different locations by receivers. This systems uses only reflected waves and disregard transmitted waves.

U.S. Pat. No. 5,640,959 describes an ultrasonic diagnostic apparatus comprising a plurality of piezoelectric transducers for sequentially transmitting and receiving ultrasonic waves. This document suggests use of a beamformer, but the beamforming delays are predefined while in this invention we compute the delays from the reference signals.

WO0230288 discloses an ultrasonic tomography method involving ultrasonic signals sequentially emitted from a set of ultrasonic transducers, and received by all transducers in parallel.

FR2862520 discloses an ultrasound beamforming probe includes an array of transducer elements and a processing board that carries a signal processor. The processor determines a beamforming phase shift derived from the spatial location for each transducer unit in the receive aperture, and applies the respective phase shift to each signal from the units. The phase shifts are not determined from the reference signals.

Ultrasound imaging beamforming apparatus comprising a transmit beamformer and a receive beamformer. The combination of signals is performed in the examined body, not through post-processing.

WO2004064619 discloses another ultrasound imaging beamformer apparatus and method. Operating in real time, i.e., not post-processed.

The content of all the previous cited patent documents is herewith included by reference.

BRIEF SUMMARY OF THE INVENTION

An aim of the invention is to propose a time of flight estimation method using a tomographic setup that consists of transmitters and receivers placed around a volume being scanned, i.e., an object whose interior is to be imaged. An acoustic signal is sent by each transmitter and received by each receiver. The sound propagation is modelled using the ray theory. We are interested in computing the sound transmission parameters, namely, the time taken by a sound wave to propagate from a transmitter to a receiver, hereafter referred to as time-of-flight. From these measurements, a sound speed image can be computed using an inverse method. The reconstruction quality of these images depends on both the accuracy of the measurements and the chosen inverse method.

There are two main problems pertaining to the measurement of time-of-flights.

First, in many applications of acoustic tomography, the signal that passes through the object of interest is highly attenuated. This results in a low signal-to-noise ratio which makes the estimation of the unknown time of flights a challenging task.

Second, part of the signal is reflected or refracted through the medium, such that it adds up to the signal of interest (the direct path) on the receiver side. In particular, a large portion of the transmitted signal travels on the surface of the object. It is thus referred to as a surface wave. These interfering signals always arrive later than the direct path but nevertheless strongly affect the signal of interest. Sometimes, these late arrivals are even less attenuated than the direct path and thus appear as dominant signals on the receiver side. This makes time delay estimation very difficult.

The aims are solved by the features of the independent claims. Advantageous embodiments are given in the dependent claims.

The aims of the invention are solved according the independent method claim by an acoustic tomography time of flight estimation method, said method comprising the steps of:

sequentially triggering a set of N transmitters so as to generate a sequence of N acoustic waves through a volume being scanned;

receiving each of said acoustic waves after transmission through said volume with a set of M receivers, which are called received signals;

delaying by varying delays the N different said received signals that each receiver receives from the N different transmitters, and adding them together to form a new received signal, which is called transmit-beamformed signal for that receiver;

delaying by varying delays the M different said transmit-beamformed signals for each receiver and adding them together at each receiver to form a new signal, which is called transmit-receive-beamformed signal.

Said volume can be a known medium, such as water, and the received signals through said known medium are called reference signals. The method can comprise a step of weighting said N different received signals and said M different transmit-beamformed signals before the addition.

Said varying delays to generate transmit-beamformed signal from a transmitter to a receiver can be computed as:
  select a set of close by transmitters around said transmitter, which is called $set_i$ transmitters;
  compute the delays that need to be applied on said received signals at said receiver from said $set_i$ transmitters based on difference between the time of flights of reference received signals at said receiver from said $set_i$ transmitters; and
  repeating both aforementioned steps, the selecting step and the computing step, for all N times M pairs of N transmitters and M receivers.

Said varying delays used to generate transmit-receive-beamformed signal from a transmitter to a receiver can as well be computed as:
  selecting a set of close by receivers around said receiver, which is called $set_j$ receivers;
  computing the delays that need to be applied on said transmit-beamformed signals for $set_j$ receivers from said transmitter based on the difference between the time of flights of reference signals from said transmitter to $set_j$ receivers; and
  repeating both aforementioned steps, the selecting step and the computing step, for all N times M pairs of N transmitters and M receivers.

According to the invention the transmit-beamformed signal from transmitter to receiver can be generated by applying said varying delays to received signals from $set_i$ transmitters to receiver and adding them together.

According to the invention the transmit-receive-beamformed signal from transmitter to receiver can be generated by applying said varying delays to transmit-beamformed signals from transmitter to $set_j$ receivers and adding them together.

The difference between the time of flights can be computed as the difference in the position of the first significant peak in said reference signals, or the difference between any other marker point in the reference signals.

The difference between the time of flights can be found by using position of the peak of the cross-correlation between said reference signals.

It can be provided a background detector for classifying as background portions of said volume through which acoustic waves can pass at the same speed as through a reference medium.

A method to compute the time of flight from transmitter to receiver by computing the difference of the time of flights between the transmit-receive-beamformed signal from transmitter to receiver and the reference signal from transmitter to receiver by any of the methods in any of the claim 8 or 9; and adding that to the time of flight computed based on the distance between the transmitter and receiver and the known sound speed of said known medium.

BRIEF DESCRIPTION OF THE DRAWINGS

The invention will be better understood with the aid of the description of an embodiment given by way of example and illustrated by the figures, in which.

DETAILED DESCRIPTION OF POSSIBLE EMBODIMENTS OF THE INVENTION

Figure 1A:
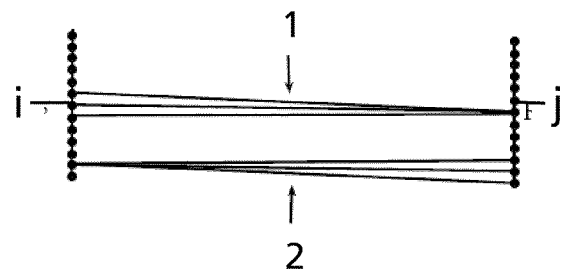
FIG. 1a shows the principles of transmitter i, receiver j beamforming and FIG. 1b an example of 3D transmit beamforming.

According to one aspect of the disclosure, one enhances the direct signal while reducing the effect of the late arrivals. Note that the strategy of simply increasing the power of the transmitted signal does not provide satisfactory results since the power of the late arrivals is increased proportionally. In the following, we propose a method to increase the signal-to-noise ratio of the direct path while significantly reduce the power of late arrivals.

Proposed Solution

In order to address the aforementioned problems, we propose to enhance the signal in a particular direction and to suppress the other directions at both transmitter and receiver sides using different types of beamforming.

Beamforming is a signal processing technique used with arrays of transmitters and receivers in order to enhance the sound wave propagating in a desired direction. When used on the receiver side, receive beamforming allows increasing the receiver sensitivity to sound waves propagating in the direction of interest, and decrease the power of signals arriving from other directions. On the transmitter side, transmit beamforming allows to focus the transmitted energy in a given direction. Therefore, beamforming techniques allow us to enhance the signal in a particular direction and suppress noise and reflections coming from other directions. To this end, we use a simple delay and sum beamformer.

Delay and sum beamforming, as its name implies, takes the set of signals, delays and possibly weights them by varying amounts, and then adds them all together. The delays are determined according to the direction (for farfield) or the point (for nearfield) at which the array or transmitters or receivers is aimed. Delay and sum beamforming allows achieving optimal noise suppression for the case of a point source in a background of white noise.

According to one aspect, the method implements both transmit and the receive beamforming. The beamforming technique is powerful but very sensitive to the delays that need to be applied to the transmitted and the received signals.

The proposed method concerns the computation of these delays. The delays of the beamforming are computed using a reference signal, which is a signal sent through a reference medium (such as water) without object, hereafter referred as reference. The advantage of the reference is that it contains no reflections, refractions or surface waves. The reference signal is preferably sent before each use of the system. We can refer to this phase as the calibration phase. The reference signals are preferably sent one by one by each transmitter and not all at the same time. Each transmitter sends his reference signal and all other receivers receive it and then we move on to the next transmitter until all the transmitters send their signals separately. If we want to do attenuation tomography, the ratio between the power of the received signal and the respective reference signal is an indication of the attenuation of the breast or object being scanned. In the following we explain how we compute the delays of the transmit and receive beamforming.

Transmit Beamforming 1

Figure 1B:
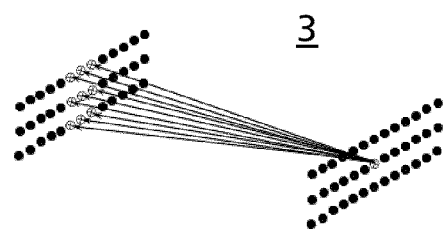

For each transmitter i-receiver j pair, we consider a set of transmitters that are close to the transmitter i, and we call them $set_i$ transmitters. At the receiver side we build a new signal that is a sum of shifted versions of the received signals from $set_i$ transmitters (see FIG. 1).

The shifts correspond to the differences in the time delays between the transmitters from $set_i$ and the receiver j, and they are computed using the reference signals from the same $set_i$ transmitters to the receiver j. By knowing the distances between the transmitters and receivers, we have a good estimate of the shifts that should be applied to the reference signals. With the help of this shift, we select the appropriate part of the received reference signals and interpolate them. To find the fine alignment, we compute the cross correlation between the reference signals and find the peaks of the correlation. The positions of the peaks correspond to the correct shifts. We can then align the received signals and compute their sum. This will be the new received signal from transmitter i to receiver j.

This process is done for all pairs of transmitters and receivers.

We remark that this is not a classical transmit beamforming in which case a group of N transmitters, e.g. $set_i$ transmitters, needs to send signals simultaneously. In our case, the transmitters can be sequentially powered, and the effect of beamforming is created in the post-processing phase (after all the signals from $set_i$ transmitters are received). This allows every transmitter to transmit at the maximum power that is defined by the safety constraints. When the N transmitters send the signals simultaneously (as in the classical transmit beamforming), the total sending power needs to be below the maximum level, what implies that each transmitter sends the signal at the power that is the maximum power divided by the number of currently active transmitters. Doing the transmit beamforming in the post-processing phase, for example by software, after reception of the N signals by each receiver, allows more energy to be sent through the object of interest and, hence, increases the signal-to-noise ration at the receiver side.

It is also possible to have transmitters emitting simultaneously, but in different frequency bands, or so as to generate N orthogonal signals that can be distinguished at reception.

Receive Beamforming 2

We can continue to enhance more the signals by doing beamforming on the receiver side.

Assume that the goal is to do receiver beamforming from transmitter i to receiver j. To enhance the signal of the receiver j, we take the signals sent by the transmitter i and received by the nearby receivers to the receiver j, called $set_j$ receivers (see FIG. 1). In order to align them with the received signal at the receiver j we again need to compute the corresponding shifts. This can be done using the corresponding reference signal and the correlation method proposed earlier. After the correct shifts are computed, we can sum the received signals and in that way obtain the new received signal for receiver j.

This procedure has to be applied to all receivers.

Fine Tuning of the Beamforming Parameters

After estimating the beamformer parameters by cross correlating the reference signals, we can fine tune the delay estimates between the received signals by doing a cross correlation between the received signals in a short time interval. These intervals are centered around the time shifts found from the reference signals. The goal of this step is to better find the shift parameters between the received signals by applying cross correlation not on the whole signal but on a short interval that hopefully contains the direct signal and not the surface wave. In this way, only the direct signal affects the fine tuning procedure and not the surface wave.

Time-Of-Flight Estimation

We estimate the time-of-flight between every transmitter and receiver by comparing the received signal when the object is present, hereafter referred as signal, with the received reference signal. Both the received signals of the signal and the reference are obtained after applying transmit and receive beamforming. We compute the time-of-flight difference between the signal and the reference. This can be done by searching for the beginning of the two signals and comparing the two positions, but sometimes it can be very difficult due to different responses of the transducers. Instead, we consider three different techniques.

Figure 2:
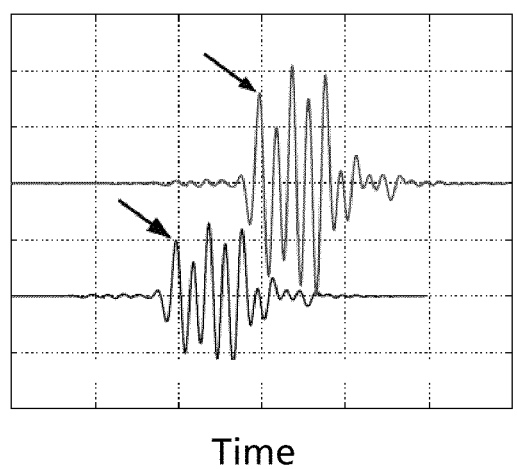
FIG. 2 shows the signal and the reference with the difference in the time of flights are determined by comparing the first significant peaks.

The first one amounts to find the first significant peak of the two signals and compare their positions (see FIG. 2). The correct time delay is then obtained as a sum of the time delay difference between the signal and the reference plus the reference time-of-flight. The latter is calculated from the known positions of the transducers and the known sound speed of the reference medium, e.g., water. If we are interested in differentiating the tissue inside the object then the reconstruction of the sound speed difference is sufficient. Otherwise, the absolute sound speed can be calculated as a sum of the difference sound speed and the sound speed of the medium.

FIG. 2 shows the signal and the reference. It is hard to determine the beginning of the signals. Since we are interested only in the time-of-flight difference we can compute the difference by comparing any other two points, chosen to be corresponding signal markers, for example the first significant peaks.

The second method amounts to find the peak of the cross correlation between the two signals. This has the advantage of taking the complete signals into account for time delay estimation. However, if the interfering signals have not been significantly reduced by the above beamforming techniques, this method may not necessarily provide the best results.

The third method is a parametric one. The effect of the medium is modelled as a linear and time-invariant filter with a few taps, each representing the attenuation and the delay introduced by one propagating path. Our method consists in retrieving this filter using the two signals. This can be achieved using reconstruction schemes based on annihilating filters, or using l1 minimization methods and associated algorithms. This filter estimation can also be done frequency-band wise to take into account for the non-linearities introduced by the considered propagation medium.

Note that the above methods can be used separately or in conjunction with the beamforming techniques explained above.

Reconstruction

Inversion Methods

We use an iterative non-linear inversion algorithm presented in "I. Jovanovic, L. Sbaiz and M. Vetterli, *Acoustic Tomography for Scalar and Vector Fields: Theory and Application to Temperature and Wind Estimation*, to appear in Journal of Atmospheric and Oceanic Technology, 2008", the content of which is herewith incorporated by reference. We thus use an algebraic reconstruction algorithm for the inversion.

The sound propagation is modelled using a bent ray model. The algorithm alternates between estimating the trajectories of sound propagation and computing the sound speed on these trajectories.

Estimating the sound speed based on the current trajectories is achieved by solving a linear system of equations. Two inversion methods are given. The first computes the mean-square optimal solution. This is achieved by minimizing the quadratic cost function using a conjugate gradient method. The second one imposes a sparsity constraint on the set of possible solutions and uses l1 minimization for reconstruction.

Results

In the following we are going to show the effect of beamforming (transmit and receive beamforming) to the signal enhancement, and on the final reconstruction.

Figure 3:
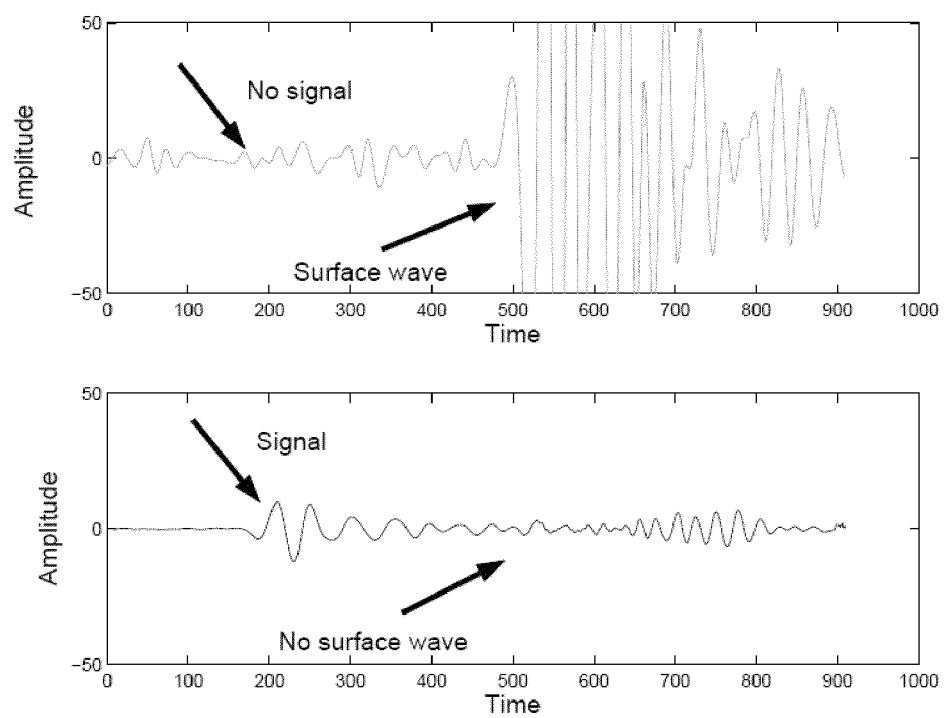
FIG. 3 shows the signal with transmit and receive beamforming (top) and without transmit and receive beamforming (bottom)
Figures 4A, 4B:
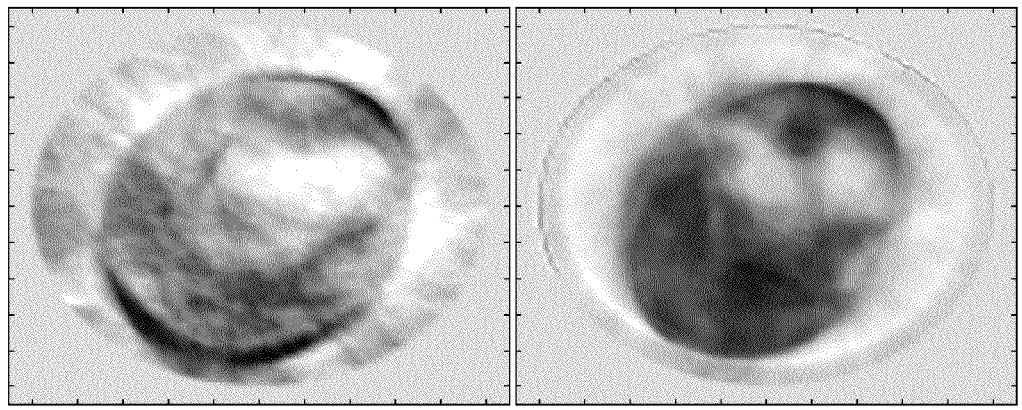
FIG. 4 shows a reconstructed speed image for the in vivo data, in FIG. 4(a) without beamforming, in FIG. 4(b) with beamforming. The effect of the surface wave disappears after the transmit and receive beamforming is applied.

FIG. 3 shows the signal before and after the beamforming, resp. the signal without (top figure) and with (bottom figure) beamforming. First, we can see that after transmit and receive beamforming the noise level is dramatically decreased. This helps in extracting the correct part of the signal which we use to compute the correct time-of-flight. At the same time the surface wave after transmit and receive beamforming is almost annihilated because the different signals that are summed in the beamformer have the late arrivals at different positions and they cancel each other. The transmit and receive beamforming will then be very useful when the signal is highly attenuated or/and the late arrivals arrives shortly after the main signal. In FIG. 4 we show the reconstruction when no beamforming is applied on the signal and when the transmit and receive beamforming is applied. We can see that since the signal that passed through the object was highly attenuated the inclusions inside the object are not well defined comparing to the image with the multi-beamforming. Also the effect of the surface wave visible on the edge of the object in FIG. 4(*a*) disappears in FIG. 4(*b*). The raw data used for the previous reconstruction are obtained by scanning one slice of a breast.

Figures 5A, 5B:
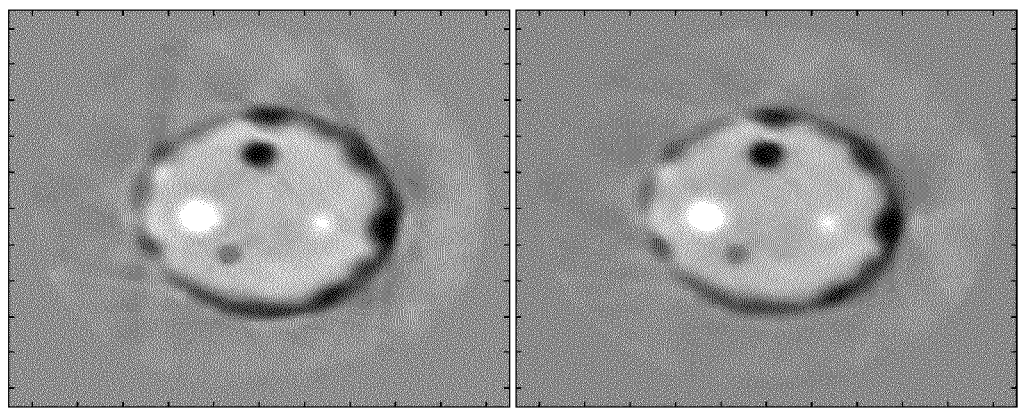
FIG. 5 shows a reconstructed speed image for the phantom data, in FIG. 5(a) without beamforming, in FIG. 5(b) with beamforming. The effect of the surface wave disappears after the transmit and receive beamforming is applied.

The same effect of removing the surface wave is visible on the phantom images shown in FIG. 5*a, b*.

Background Removal

Automatic detection and removal of the background, for example water or another reference medium, has two positive effects. First there is a visual effect, since it brings forth the object of interest. More importantly, background detection (notice, the background has a known sound speed) can be included in the reconstruction process to: 1) reduce the number of unknowns; 2) stabilize the inverse method, and 3) speed up the reconstruction. In order to detect the background, we propose a completely new approach. The idea is that by looking at the time-of-flight of a specific ray we can immediately say if that ray passed only through the water or not. The tessellation cells through which the specific ray passed are then possible candidates for the background set. Examining every ray for which the time-of-flight is equal or very close to the time-of-flight through water, or equivalently the reference, we can obtain the background cell set. To exclude the special cases in which the presence of an inclusion inside the object can result in the same time-of-flight as for the water, we can additionally impose that the background set is simply connected. Another condition can be that the cell is qualified as a background cell by more than a prescribed number of ray.

The invention claimed is:

1. An acoustic tomography method to improve the time of flight estimation, the method being performed with a tomography set up which comprises transmitters and receivers located around a volume to be scanned, said method comprising the steps of:

sequentially triggering a set of N transmitters so as to generate a sequence of N acoustic waves which are passed completely through a volume being scanned;

receiving each of said acoustic waves after transmission through said volume with a set of M receivers, which are called received signals;

delaying by varying delays the N different said received signals that each receiver receives from the N different transmitters, and adding them together to form a new received signal, which is called transmit-beamformed signal for one of the M receivers, such that the transmit-beamformed signal is focused onto a focal point located at said one receiver, wherein said varying delays used to generate said transmit-beamformed signal from a transmitter to a receiver are computed as:

(i) selecting a set of close by transmitters around said transmitter, which is called $set_i$ transmitters (ii) passing a reference signal from the $set_i$ transmitters completely through a reference medium which does not reflect the reference signal, to the receiver;

(iii) computing the delays that need to be applied on said received signals at receiver from said $set_i$ transmitters based on difference between the time of flights of reference received signals at said receiver from said $set_i$ transmitters, and (iv) repeating both aforementioned steps, the selecting step and the computing step, for all N times M pairs of N transmitters and M receivers;

delaying by varying delays the M different said transmit-beamformed signals for each receiver and adding them together at each receiver to form a new signal, which is called transmit-receive-beamformed signal for one of the N transmitters, such that the transmit-receive-beamformed signal is focused onto a focal point located at said one transmitter, wherein said varying delays used to generate transmit-receive-beamformed signal from a transmitter to a receiver is computed as:

(i) selecting a set of close by receivers around said receiver, which are called $set_j$ receivers;

(ii) passing reference signal from transmitted completely through a reference medium which does not reflect the reference signal, to the $set_j$ receivers;

(iii) computing the delays that need to be applied on said transmit-beamformed signals for $set_j$ receivers from said transmitter based on the difference between the time of flights of reference signals from said transmitter to $set_j$ receivers; and (iv) repeating both aforementioned steps, the selecting step and the computing step, for all N times M pairs of N transmitters and M receivers;

calculating the time of flight by determining the time difference between the transmit-receive-beamformed signal and a reference signal.

2. The method of claim 1, comprising a step of weighting said N different received signals and said M different transmit-beamformed signals before the addition.

3. The method of claim 1, where the transmit-beamformed signal from said transmitter to said receiver is generated by applying said varying delays to received signals from $set_i$ transmitters to receiver and adding them together.

4. The method of claim 1, where the transmit-receive-beamformed signal from said transmitter to said receiver is generated by applying said varying delays to transmit-beamformed signals from transmitter to $set_j$ receivers and adding them together.

5. The method of claim 1, wherein the difference between the time of flights are computed as the difference in the position of the first significant peak in said reference signals, or the difference between any other marker point in the reference signals.

6. The method of claim 1, wherein the difference between the time of flights is found by using position of the peak of the cross-correlation between said reference signals.

7. The method of claim 1, comprising a background detector for classifying as background portions of said volume through which acoustic waves pass at the same speed as through a reference medium.

8. A method to compute the time of flight from a transmitter to a receiver by computing the difference of the time of flights between the transmit-receive-beamformed signal from said transmitter to a receiver and the reference signal from said transmitter to said receiver by the method in claim 5; and adding that to the time of flight computed based on the physical distance between the transmitter and receiver and the known sound speed of said known medium.

* * * * *